United States Patent [19]
Molnar et al.

[11] Patent Number: 5,836,225
[45] Date of Patent: *Nov. 17, 1998

[54] METHOD AND APPARATUS FOR PROCESSING CHOPPED FIBERS FROM CONTINUOUS TOWS

[75] Inventors: Julius J. Molnar, Amherst; Gregory Alaimo, Avon Lake, both of Ohio; John M. Raterman, Lawrenceville, Ga.

[73] Assignee: Nordson Corporation, Westlake, Ohio

[ * ] Notice: The term of this patent shall not extend beyond the expiration date of Pat. No. 5,450,777.

[21] Appl. No.: 490,547

[22] Filed: Jun. 15, 1995

Related U.S. Application Data

[62] Division of Ser. No. 801,907, Dec. 3, 1991, Pat. No. 5,450,777.

[51] Int. Cl.$^6$ .............................. D01G 1/04; B26D 1/28
[52] U.S. Cl. .................... 83/100; 83/74; 83/168; 83/356.1; 83/356.3; 83/443; 83/444; 83/592; 83/694; 83/913
[58] Field of Search ................... 83/24, 62, 72, 83/98, 168, 356.1, 356.3, 358, 364, 365, 367, 402, 436, 913, 923, 592, 607, 675, 694, 74, 100, 443, 444; 226/110, 186; 425/196

[56] References Cited

U.S. PATENT DOCUMENTS

| | | | |
|---|---|---|---|
| 160,121 | 2/1875 | Robert | 83/675 X |
| 887,205 | 5/1908 | Locke | 83/592 X |
| 2,217,766 | 10/1940 | Neff | 83/913 X |
| 2,581,467 | 1/1952 | Bailiff et al. | 83/913 X |
| 2,696,881 | 12/1954 | Krueger | 83/98 |
| 3,831,482 | 8/1974 | Eichler et al. | 83/675 |
| 3,986,417 | 10/1976 | Anderson, Jr. et al. | 83/913 X |
| 4,188,845 | 2/1980 | Stukenberg | 83/913 X |
| 4,251,198 | 2/1981 | Altenburg | 83/675 X |
| 4,285,652 | 8/1981 | Anders | 425/313 X |
| 4,655,111 | 4/1987 | Blaker et al. | 83/913 X |
| 4,698,009 | 10/1987 | Marin et al. | 425/196 |
| 4,728,276 | 3/1988 | Pauley et al. | 425/67 |
| 5,450,777 | 9/1995 | Molnar et al. | 83/98 |

FOREIGN PATENT DOCUMENTS

| | | | |
|---|---|---|---|
| 1660180 | 1/1972 | Germany | 83/913 |
| 114615 | 9/1981 | Japan | 83/356.1 |

*Primary Examiner*—Rinaldi I. Rada
*Assistant Examiner*—Clark F. Dexter
*Attorney, Agent, or Firm*—Wood, Herron & Evans L.L.P.

[57] ABSTRACT

Apparatus for processing chopped fibers from essentially continuous tows, each consisting of individual strands, comprises independently or selectively feeding at least two tows to a venturi pump and associated cutter mechanism where the tows are cut or chopped into relatively short lengths to form chopped fibers. The apparatus includes sensors for monitoring the movement of each of the tows to the pump and cutter mechanism, and a controller which adjusts the feed rate of the tows and the rate of operation of the cutter mechanism in the event movement of one of the tows varies from a predetermined feed rate.

15 Claims, 7 Drawing Sheets

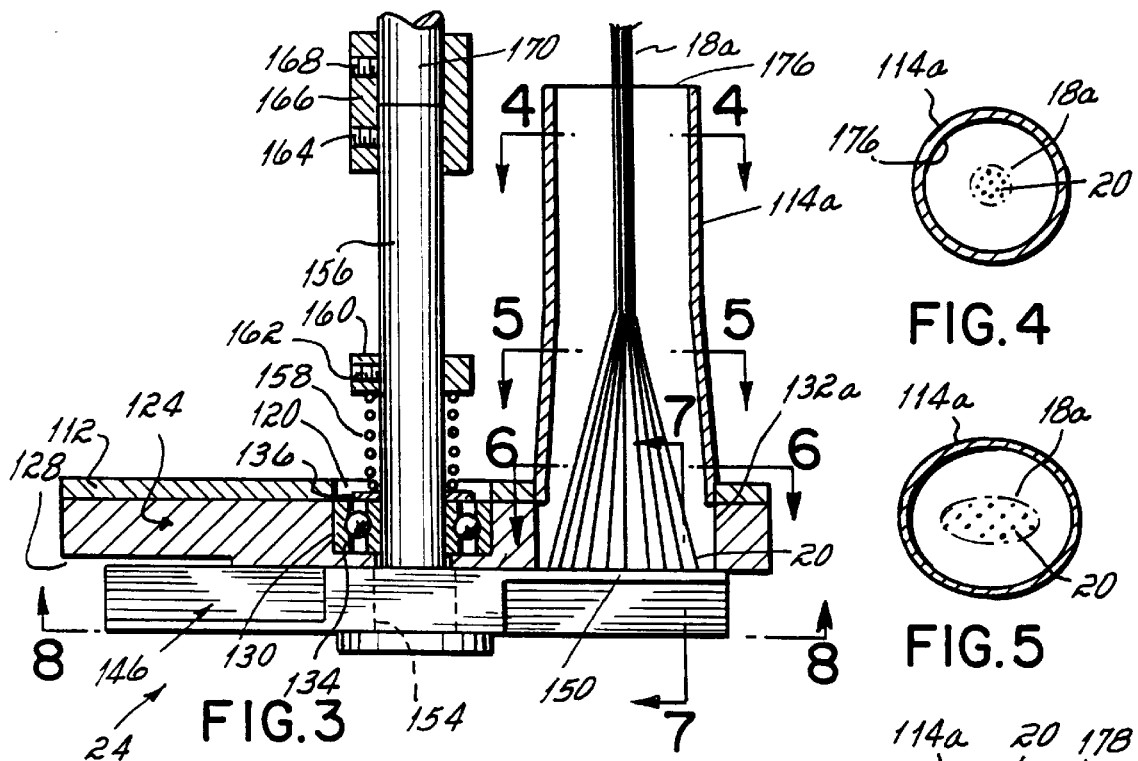
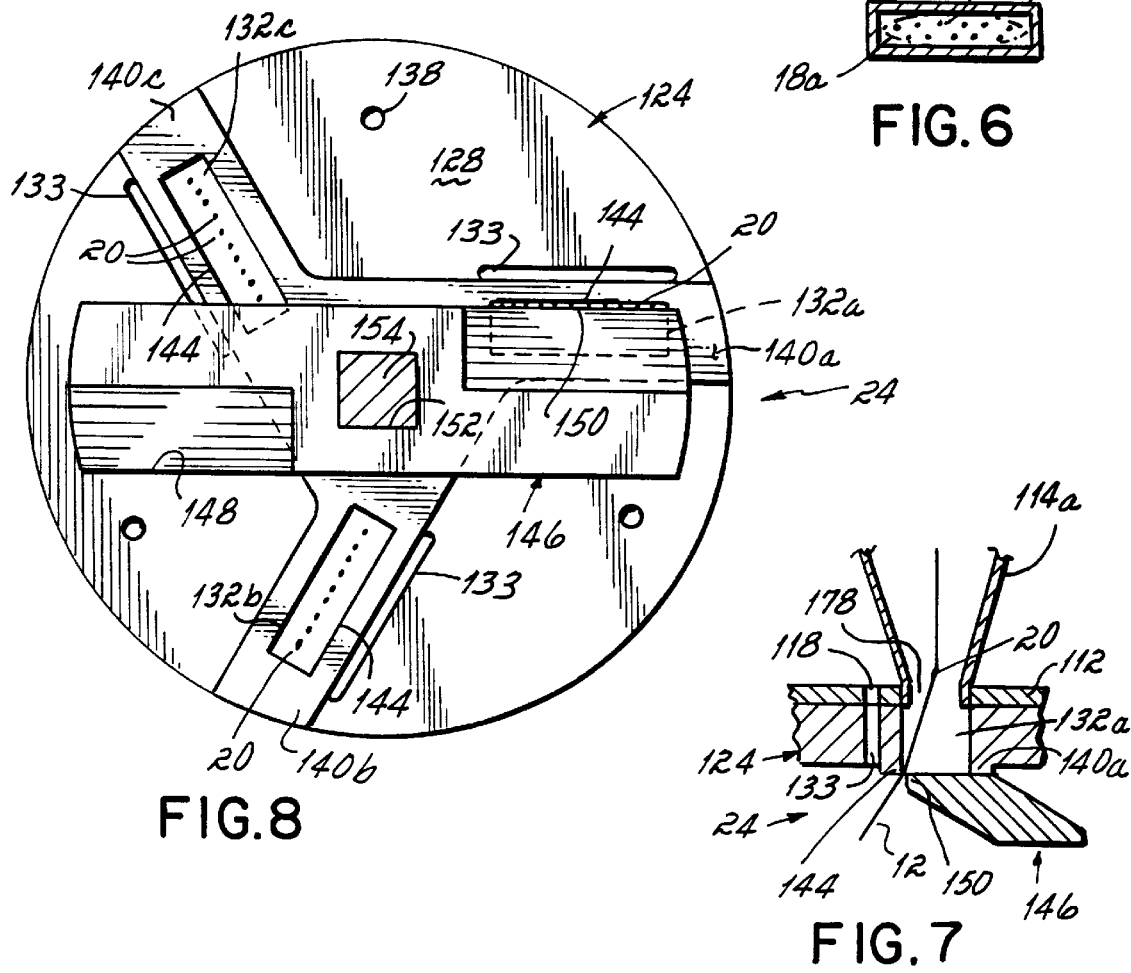

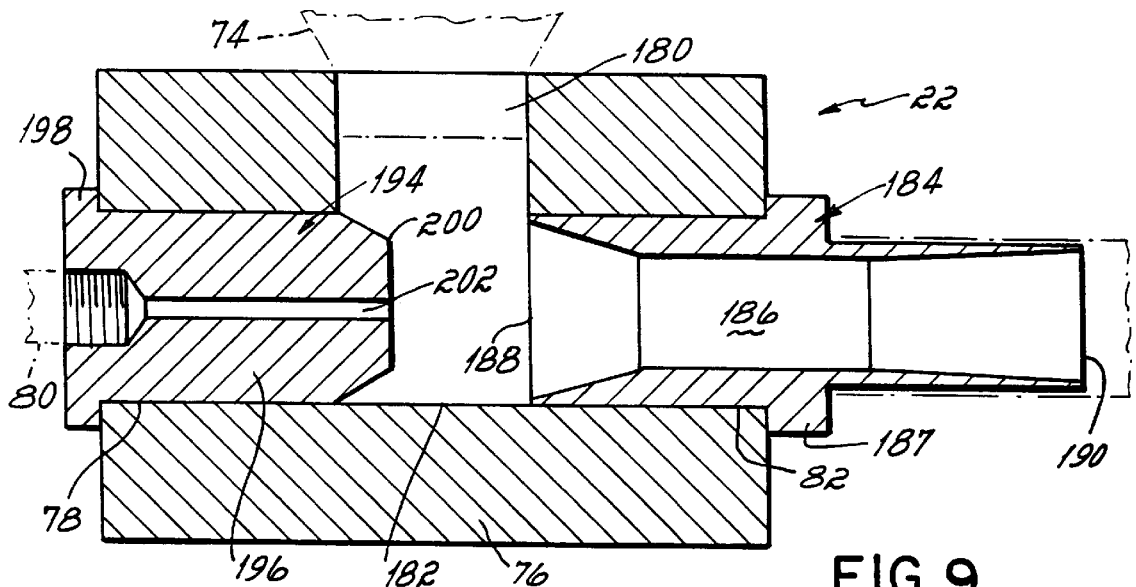
FIG. 9
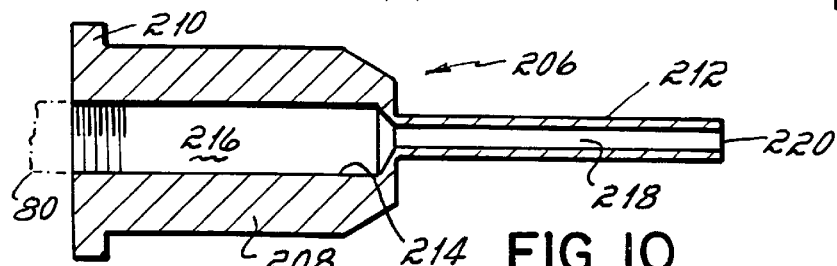
FIG. 10
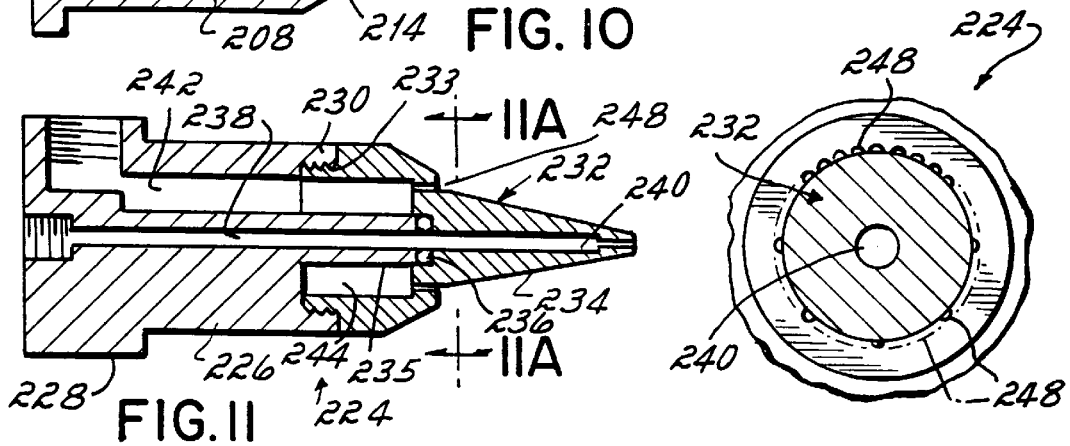
FIG. 11
FIG. 11A
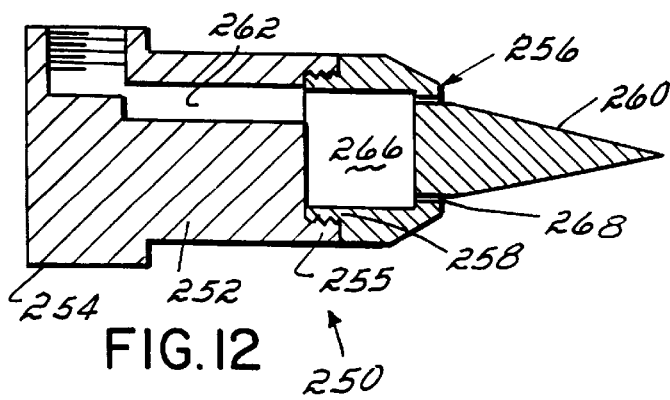
FIG. 12
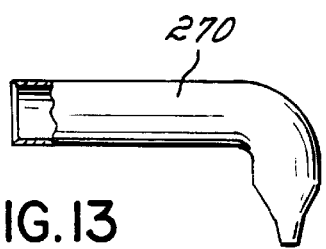
FIG. 13

METHOD AND APPARATUS FOR PROCESSING CHOPPED FIBERS FROM CONTINUOUS TOWS

This application is a DIVISIONAL of application Ser. No. 07/801,907 filed Dec. 3, 1991, now U.S. Pat. No. 5,450,777.

FIELD OF THE INVENTION

This invention relates to an apparatus for processing chopped fibers, and, more particularly, to a method and apparatus for chopping or cutting one or more essentially continuous tows, each consisting of individual strands, into relatively short fibers of predetermined length which are dispensed at an accurately controlled feed rate onto or into a substrate such as the nonwoven pad of a hygienic article.

BACKGROUND OF THE INVENTION

Hygienic articles such as disposable diapers, sanitary napkins, incontinence pads and sick bed sheets must have a high absorption capacity to effectively retain eliminated body fluids for acceptable periods of time. Early hygienic articles of this type employed cellulose wadding, fluff cellulose or absorbent cotton as absorbent materials. The problem with these materials is that their moisture-retaining capacity is relatively small compared to their volume. In order to improve the moisture-retaining capacity of hygienic articles made from these materials, the volume of such absorbent materials in the hygienic article must be increased. This produces a bulky product which is unacceptable in many hygienic articles, particularly sanitary napkins.

In an effort to reduce the volume and size of hygienic articles, and increase their absorbent capacity, fluid absorbent substrates have been developed in which highly absorbent materials are combined within the fiber structure of cellulose fluff, wood pulp, textile fibers or other nonwoven fibrous materials. Many substantially water-insoluble absorbent polymers having a high capacity for absorbing water and body fluids have been developed in recent years for enhancing the moisture-absorbent capability of hygienic articles. These polymers are partially or wholly synthetic and are commercially available in fine grain, particulate form or in continuous tows consisting of a number of individual strands. See, for example, U.S. Pat. Nos. 3,997,484; 3,661,815; 4,117,222; and, 3,936,441.

A number of systems have been developed for incorporating a moisture-absorbent material in the nonwoven layer or pad of a hygienic article, such as a disposable diaper, as discussed in U.S. Pat. Nos. 4,927,346 and 5,017,324 owned by the assignee of this invention. In the particular system disclosed in Pat. No. 4,927,346 and 5,017,324, highly moisture-absorbent material in fine grain particulate form is incorporated within the nonwoven pad of a hygienic article within a forming chamber. A perforated conveyor is movable between the inlet and outlet of the forming chamber above a duct which is connected to a source of vacuum. Nonwoven fibers formed of cellulose fluff, wood pulp or other nonwoven materials are introduced into the forming chamber through a conduit and drawn onto the perforated conveyor by operation of the vacuum source. As the nonwoven material is drawn atop the conveyor, one or more spray guns located within the forming chamber intermix the highly moisture-absorbent material with a portion of the fibrous, nonwoven material to form a nonwoven pad having moisture-absorbent material interspersed throughout a predetermined portion of its thickness while leaving other portions of the pad substantially free of highly moisture-absorbent material. In the formation of a disposable diaper, for example, the nonwoven pad containing the moisture-absorbent material is subsequently attached to a thin layer of polyethylene which forms the backing sheet of the finished article.

Currently available hygienic articles, such as disposable diapers, are manufactured with systems of the type described above using highly moisture-absorbent material in fine grain, particulate form. Despite efforts to locate the highly moisture-absorbent particulate material at selected areas within the thickness of a nonwoven pad of such articles, there have nevertheless been problems attributable to the form of the moisture-absorbent material. It has been found that the particles of highly moisture-absorbent material tend to sift through the nonwoven fibers of the nonwoven pad and can be lost through the perforated conveyor within the forming chamber. Particulate, moisture-absorbent material is difficult to contain, even with a filtering system associated with the forming chamber, and environmental contamination can result. Sifting or migration of particulate moisture-absorbent material through the nonwoven fibers is also a problem within the finished hygienic article. It is not uncommon for the moisture-absorbent particles to sift through the nonwoven layer and concentrate at the polyethylene backing sheet of a disposable diaper, for example, producing an undesirable rough, granular feel to the diaper.

Another problem with the use of highly moisture-absorbent material in granular or particulate form within hygienic articles is the speed at which it absorbs urine or other body fluids. While capable of absorbing moisture many times its weight, particles of highly moisture-absorbent material have a relatively small surface area and body fluids must come into contact with such particles in order to be absorbed. Even if a relatively large quantity of particulate moisture-absorbent material is provided within a hygienic article, there are nevertheless spaces or areas within the nonwoven pad with lesser concentrations of particles and therefore a longer time period is required before such moisture or bodily fluids can be absorbed.

SUMMARY OF THE INVENTION

It is therefore among the objectives of this invention to provide a method and apparatus for depositing highly moisture-absorbent material into the nonwoven layer or pad of hygienic articles such as disposable diapers which substantially reduces loss of moisture-absorbent material, which eliminates unwanted migration of moisture-absorbent material within the finished article, which provides for rapid absorbency of bodily fluids or other moisture and which provides an accurately metered volume of moisture-absorbent material.

These objectives are accomplished in a method and apparatus for forming chopped fibers of highly moisture-absorbent material from essentially continuous tows each consisting of individual strands of moisture-absorbent material. At least two tows are independently fed to a venturi pump and associated cutter mechanism where the tows are cut or chopped into relatively short lengths to form chopped fibers, and are then discharged to a forming chamber, for example, of the type disclosed in U.S. Pat. Nos. 4,927,346 and 5,017,324. The apparatus includes sensors for monitoring the movement of each of the tows to the pump and cutter mechanism, and a controller which adjusts the feed rate of the tows and the rate of operation of the cutter mechanism in the event movement of one of the tows is interrupted or discontinued.

In the presently preferred embodiment of this invention, a total of three tows are supplied from separate containers or hoppers to a primary feed roller rotated by a variable speed motor. Each of the tows is forced against the feed roller by a separate pressure roller which is movable between an extended position in which it engages the feed roller and a retracted, disengaged position. Each tow is individually advanced from the primary feed roller to a secondary feed roller, driven by a variable speed motor, at which a second set of pressure rollers, one for each tow, is provided. The tows are advanced from the secondary feed roller into separate guide tubes of a cutter mechanism located at the inlet of the venturi pump, which applies a continuous negative pressure to the tows. As described below, each tow is cut into chopped fibers of uniform length by the cutter mechanism and then discharged from the pump into, for example, the forming chamber for the nonwoven pad of a hygienic article.

The primary and secondary feed rollers are rotated by their respective variable speed motors at a predetermined rate, corresponding to the line speed of the hygienic article line, for example, to ensure that an accurately metered quantity of chopped fibers of highly moisture-absorbent material is provided. The cutter mechanism has a cutter blade mounted to the drive shaft of a third variable speed motor which is operative to control the speed of rotation of the cutter blade in timed relation to the feed rate of the tows from the secondary feed roller. The feed rate of the tows into the cutter mechanism, and the speed of rotation of the cutter blade, determine the length of the fiber tows discharged from the pump.

One important aspect of this invention is the provision of sensing devices and control means to ensure that a substantially constant feed rate or volume of chopped fibers of uniform length is maintained, even if the supply of one or more of the tows is slowed, interrupted, discontinued or otherwise varied for any reason. This is particularly desirable in the application of introducing highly moisture-absorbent material into the nonwoven pad of hygienic articles where the quantity of moisture-absorbent material must be closely controlled and high production speeds require minimal interruption in the supply of moisture-absorbent material.

In the presently preferred embodiment, sensors are provided upstream from the primary feed roller to detect the movement of each of the tows thereto. Another set of sensors is provided between the primary and secondary feed rollers to sense the presence and movement of the tows therebetween, and additional sensors are placed at the inlet to the cutter mechanism. In the event any one of these sensors detects an absence of movement, movement of one or more of the tows below a predetermined rate or any other variation in feed rate, an operational sequence is initiated to ensure that the quantity of the fibers discharged from the venturi pump remains substantially unchanged.

For example, assuming the movement of one of the three tows is interrupted or stopped for some reason, a controller operates to move each of the two pressure rollers associated with that tow, i.e., one at each of the primary and secondary feed rollers, to a retracted position away from such feed rollers. A clamping mechanism associated with such tow, located between the secondary feed roller and the venturi pump, is then activated to clamp such tow in a fixed position. In order to make up for the reduced volume of material entering the cutter mechanism and venturi pump due to the absence of one tow, the controller operates the variable speed motors to increase the speed of rotation of both the primary and secondary feed rollers so that the remaining two tows are advanced to the cutter mechanism and venturi pump at a higher rate of speed. At the same time, the controller operates the third variable speed motor to increase the speed of rotation of the cutter blade at a rate corresponding to the faster pace at which the two tows are being delivered to the cutter mechanism. As a result, the cutter mechanism cuts each of the remaining two tows to form chopped fibers having substantially the same length as those previously formed with the three tow supply, and the overall volume or quantity of chopped fibers discharged from the venturi pump is maintained substantially constant because of the increased feed rate of the remaining two tows.

In the particular application of forming the nonwoven pad of a disposable diaper, it is advantageous to deposit the highly moisture-absorbent material at longitudinally spaced locations along the nonwoven pad. This is accomplished in the system of this invention by the operation of the primary and secondary feed rollers herein. Preferably, a loop or excess length of each tow is allowed to form between the primary feed roller and a secondary feed roller so that the tension of the tows into the secondary feed roller can be controlled. In order to obtain an intermittent supply of chopped fibers into the forming chamber for the nonwoven pad of the hygienic article, the secondary feed roller is preferably rotated intermittently, i.e., its rotation is quickly started and stopped by the associated variable speed motor, so that the supply of the tows to the cutter mechanism and venturi pump is discontinuous. The venturi pump is continually operated, or, alternatively, can be started and stopped with the secondary feed rollers, so that a vacuum is applied to the tows fed thereto. As a result, the chopped fibers are discharged from the outlet of the venturi pump in accordance with the rate at which the tows are advanced from the secondary feed roller.

In another aspect of this invention, the venturi pump and associated cutter mechanism are constructed to chop or cut the individual strands of each tow to form chopped fibers of substantially uniform length, and to smoothly transmit these chopped fibers without bunching up through the venturi pump. In the presently preferred embodiment, the venturi pump comprises a pump body formed with an inlet passageway and an intersecting throughbore having opposed ends. A nozzle is mounted at one of the ends of the throughbore having an inlet adapted to connect to a source of pressurized air, and an outlet which discharges the pressurized air generally perpendicularly to the inlet passageway of the pump body and into a venturi passageway which forms the outlet of the venturi pump. A number of nozzle constructions are disclosed in the following detailed description, each of which creates a vacuum or negative pressure within the inlet passageway of the pump body to draw the tows from the secondary feed roller into the cutter mechanism and to smoothly convey the chopped fibers formed by the cutting mechanism through the venturi passageway and out of the pump body.

The cutting mechanism of this invention is mounted to the pump body of the venturi pump in communication with its inlet passageway. In the presently preferred embodiment, the cutting mechanism includes a tapered, tow guide tube for each of the tows which communicate with separate tow slots formed in a cutter plate. The tow guide tubes taper inwardly from a larger diameter inlet end to a substantially rectangular-shaped outlet end having the same cross section as the tow slots in the cutter plate. In the course of movement through the tow guide tubes into the tow slots, each tow is "opened" or spread from a generally circular cross section to a rectangular cross section in which the individual strands of each tow are located substantially side-by-side with at least some spacing therebetween. This opening or spreading of the tow is attributable not only to the shape of the tow guide tubes, but also to a pressure differential created between the tow guide tubes and the area within the cutting mechanism at which the tows are cut.

Preferably, three extensions or ribs are formed at the base of the cutter plate and a tow slot is formed in the cutter plate at each rib. A double-edged cutter blade is mounted at the end of the shaft of the third variable speed motor in position where its two cutting edges are rotated immediately adjacent the tow slots in the ribs of the cutter plate. Each fiber tow is directed through the guide tubes and tow slots in the cutter plate such that a portion of the tows extend below the ribs of the cutter plate where they are sheared by the cutting edges of the cutter blade. Because the tows are flattened or opened by the tow guide tubes, most of the individual strands in each tow are directly contacted and cut by the cutter blade, instead of being hidden behind one other, which results in a clean, accurate separation of the strands from the remainder of the tow. This aids in producing chopped fibers having substantially uniform length.

In the particular application of forming chopped fibers from tows of highly moisture-absorbent material, the individual strands forming each tow are relatively lightweight and difficult to smoothly transfer without bunching up from the area at which they are cut to the outlet of the pump. In order to obtain a smooth transfer of the tows and chopped fibers through the pump, the cutter plate and cutter blade of the cutting mechanism herein are designed to control the vacuum applied to the tows during the cutting operation and provide a flow path away from the area of the cutter blade toward the pump outlet. As mentioned above, the bottom of the cutter plate is formed with three outwardly extending ribs each formed with a rectangular-shaped tow slot which define opposed, elongated shear edges. The individual strands of each tow are simultaneously cut at these shear edges in the ribs as a cutting edge of the cutter blade moves therepast. Unlike the cutting action of a pair of scissors, for example, the cutter blade of this invention is movable with respect to the tow slots of each rib such that each cutting edge of the cutter blade is substantially parallel to one of the opposed shear edges of the tow slot at the time such cutting edge contacts the strands of a tow. As this cutting operation occurs, the remainder of the tow slot in the rib is covered by the cutting blade. This momentarily interrupts the application of vacuum upstream from the cutter plate, i.e., within the tapered guide tubes of the cutting mechanism, which ensures that the newly formed chopped fibers are cleanly separated from the remainder of the tow and immediately directed away from the cutter plate and cutter blade along a flow path leading into the venturi outlet of the pump. This feature of the present invention provides for smooth handling of the chopped fibers, and substantially prevents their bunching up within the tow slots in the cutter plate at the time of separation from the remainder of the tow, or in the course of passage from the area of the cutter plate to the outlet of the pump.

DESCRIPTION OF THE DRAWINGS

The structure, operation and advantages of the presently preferred embodiment of this invention will become further apparent upon consideration of the following description taken in conjunction with the accompanying drawings, wherein:

FIG. 3 is a cross sectional view of a portion of the cutter mechanism illustrating the passage of one tow therethrough;

FIG. 4 is a cross sectional view of one tow taken generally along line 4—4 of FIG. 3;

FIG. 5 is a cross sectional view of the tow of FIG. 4 taken generally along line 5—5 of FIG. 3;

FIG. 6 is a cross sectional view of the tow of FIGS. 4 and 5 taken generally along line 6—6 of FIG. 3;

FIG. 7 is a cross sectional view taken generally along line 7—7 of FIG. 3 showing a tow cutting operation;

FIG. 8 is a bottom view of the cutter plate and cutter blade taken generally along line 8—8 of FIG. 3;

FIG. 9 is a cross sectional view taken generally along line 9—9 of FIG. 2 showing a portion of the venturi pump herein;

FIG. 10 is a cross sectional view of an alternative embodiment of a nozzle for use with the venturi pump shown in FIG. 9;

FIG. 11 is an alternative embodiment of the nozzle shown in FIGS. 9 and 10;

FIG. 11A is a cross sectional view taken along lines 11A—11A of FIG. 11;

FIG. 12 is a still further embodiment of a nozzle adapted for use with the venturi pump of FIG. 9;

FIG. 13 is a view of an outlet tube, in partial cross section, insertable within the outlet in the pump body of FIG. 9;

DETAILED DESCRIPTION OF THE INVENTION

Figure 1:
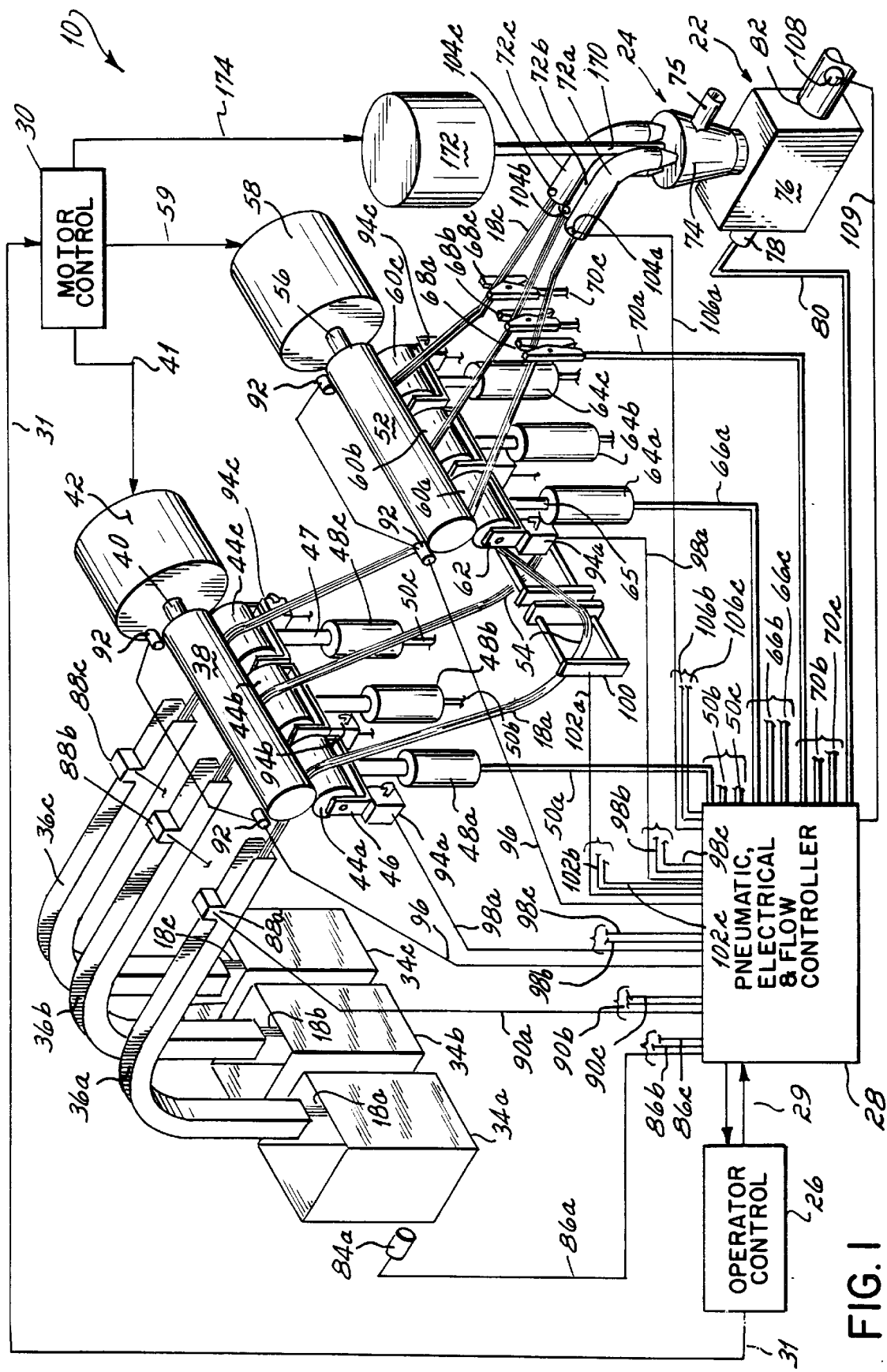
FIG. 1 is a schematic view of the overall apparatus of this invention.

One presently preferred embodiment of the chopped fiber processing apparatus 10 of this invention is schematically illustrated in FIG. 1. As discussed in more detail below in connection with a description of FIGS. 14–16, the apparatus 10 herein can be particularly adapted to intermix chopped fibers 12 of a highly moisture-absorbent material within a predetermined portion of the thickness of a nonwoven layer or pad 14 of a hygienic article such as a disposable diaper. For purposes of the present discussion, the structure and method of operation of apparatus 10 is described in conjunction with the formation of chopped fibers 12 from tows 18a, b and c each formed of essentially continuous, individual strands 20 (see FIGS. 6 and 7) of highly moisture-absorbent material of the type disclosed, for example, in U.S. Pat. Nos. 3,997,484; 3,661,815; 4,117,222; and, 3,936,441. It should be understood, however, that the apparatus 10 of this invention could be employed with a variety of materials and is capable of producing chopped or cut sections or fibers of relatively short length from an essentially continuous supply of material such as graphite, aramid, fiberglass and the like in the form of a tow, roving, strand or the like. The following discussion of the operation of the apparatus 10 is therefore not limited to the formation of chopped fibers of highly moisture-absorbent material for use in manufacturing disposable diapers, but is useful in a variety of other, non-hygienic article applications.

The overall construction of apparatus 10 is initially described, followed by a discussion of the venturi pump 22 and cutter mechanism 24 of the apparatus 10.

OVERALL CONSTRUCTION OF EMBODIMENT OF FIG. 1

Referring to FIG. 1, the apparatus 10 comprises an operator control 26, a combined pneumatic, electrical and flow controller 28 connected by line 29 to operator control 26, a motor control 30 connected by line 31 to operator control 26 and various tow handling and sensing devices described individually below. The operator control 26 comprises essentially an interface between the controller 28, motor control 30 and the manufacturing line to which the chopped fibers 12 are directed from the venturi pump 22. In the particular example of the formation of disposable diapers, for example, the operator control 26 provides an interface between the controller 28, motor control 30 and a conveyor 32 upon which the nonwoven layer or pad 14 of the disposable diaper is formed as described below. See FIG. 14. This interface is necessary in order to ensure that the feed rate or volume of chopped fibers 12, and the length of such fibers 12, is maintained substantially constant regardless of the speed of operation of the conveyor 32.

In the presently preferred embodiment, the three tows 18a, b, c are supplied from separate tow hoppers 34a, b, c through individual feed channels 36a, b, c to a primary feed roller 38. The primary feed roller 38 is connected to the drive shaft 40 of a variable speed, primary motor 42 which is connected by control line 41 to the motor control 30. Each of the tows 18a, b, c is fed between the primary feed roller 38 and pressure rollers 44a, b, c, respectively. These pressure rollers 44a, b, c are each carried by a separate bracket 46 and are connected to the cylinder rod 47 of pneumatic cylinders 48a, b, c, respectively. The pneumatic cylinders 48a, b, c are each connected by a separate air line 50a, b, c, respectively, to controller 28, and their cylinder rods 47 are movable between an extended position in which the pressure rollers 44a, b, c force the tows 18a, b, c against the primary feed roller 38, and a retracted position in which the pressure rollers 44a, b, c are each spaced from the primary feed roller 38.

The tows 18a, b, c are transmitted from the primary feed roller 38 to a secondary feed roller 52. Preferably, an excess length or loop 54 of each of the tows 18a, b, c is permitted to form between the primary and secondary feed rollers 38, 52 to control the tension of the tows 18a, b, c as they enter the secondary feed roller 52 for purposes described below. The secondary feed roller 52 is connected to the drive shaft 56 of a variable speed, secondary motor 58 whose operation is controlled via line 59 by motor control 30. Each of the tows 18a, b, c are independently or selectively driven at the secondary feed roller 52 in the same manner as described above in connection with the primary feed roller 38. Three pressure rollers 60a, b, c are mounted on separate brackets 62 beneath the secondary feed roller 52 in a position to engage the tows 18a, b, c, respectively. The pressure rollers 60a, b, c are moved between an extended position in which they force tows 18a, b, c against the secondary feed roller 52, and a retracted position spaced from secondary feed roller 52, by operation of pneumatic cylinders 64a, b, c, respectively, each having a cylinder rod 65 connected to a pressure roller 60a, b, c. The pneumatic cylinders 64 are operatively connected by a pneumatic lines 66a, b, c to the controller 28.

With the pressure rollers 60a, b, c in an extended position, the tows 18a, b, c are advanced from the secondary feed roller 52 and positively drawn into the cutter mechanism 24 by a vacuum or negative pressure developed within the venturi pump 22. In the presently preferred embodiment, pneumatic clamps 68a, b, c, illustrated schematically in FIG. 1, are interposed between the secondary feed roller 52 and cutter mechanism 24. These pneumatic clamps 68a, b, c are connected by separate pneumatic lines 70a, b, c to the controller 28 and are selectively operative to clamp tows 18a, b, c, respectively, in a fixed position for purposes to become apparent below. The tows 18a, b, c pass through clamps 68a, b, c and enter individual tow inlet tubes 72a, b, c, respectively, which are connected to an inlet cone 74 housing the cutter mechanism 24 described below. This inlet cone 74 is mounted to the pump body 76 of the venturi pump 22, which also includes an air inlet 78 connected by an air line 80 to the controller 28 and a chopped fiber outlet 82.

As described below in connection with a discussion of the operation of apparatus 10, an important aspect of this invention is the provision of structure for sensing the movement of each of the tows 18a, b, c through the apparatus 10 from the tow hoppers 34a, b, c to the venturi pump 22. A number of sensor devices are provided for this purpose which are located at various positions along the run of the tows 18a, b, c through apparatus 10. Beginning at the lefthand side of FIG. 1, each of the tow hoppers 34a, b, c is provided with a level sensor 84, one of which, 84a is schematically depicted. Each level sensor 84 is operative to sense the level of the tows 18a, b, c within the respective hoppers 34a, b, c, and send a corresponding signal through separate lines 86a, b, c to the controller 28. One presently preferred level sensor 84 is commercially available from Nordson Corporation of Amherst, Ohio, the assignee of this invention, under Model No. 601371.

Figure 9A:
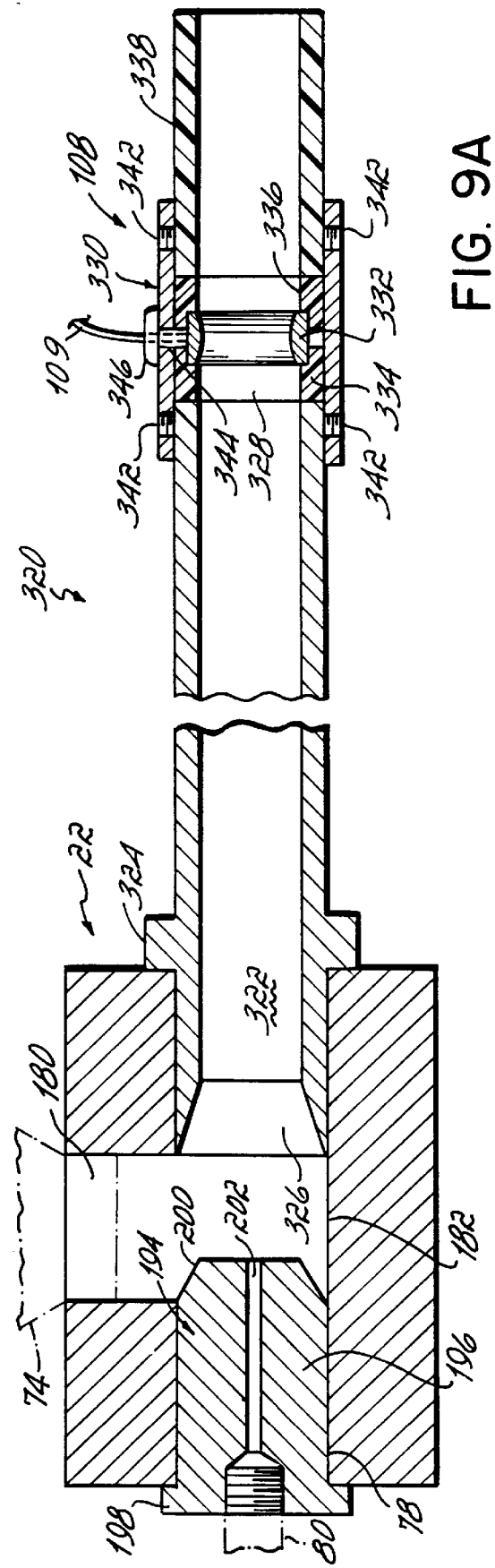
FIG. 9A is a view similar to FIG. 9 with the addition of a flow sensor to sense the movement of fibers therethrough.

Immediately upstream from the primary feed roller 38 are movement sensors 88a, b, c, preferably mounted to the feed channels 36a, b, c, respectively, associated with the tows 18a, b, c. Each of these movement sensors 88a, b, c is connected by a separate line 90a, b, c, respectively, to the controller 28 and is operative to provide a signal to the controller 28 in the event the speed of a tow 18a, b, c moving therepast falls below a predetermined feed rate. One type of movement sensor which is suitable for use herein is depicted in FIG. 9A, and is described below in connection with a discussion of the structure and operation of venturi pump 22.

The individual strands 20 forming the tows 18a, b, c (see FIGS. 4–6) are lightweight and relatively "fluffy" in their commercially available form. Preferably, the primary and secondary feed rollers 38, 52, as well as the pressure rollers 44a, b, c and 60a, b, c, are coated with a non-stick surface to discourage adherence of any of the tow strands 20 thereto. Nevertheless, it is contemplated that at least some of the strands 20 may adhere either to the feed rollers 38, 52 or pressure rollers 44, 60 at some point during the operation of apparatus 10. Material build-up sensors 92 are therefore provided at both the primary feed roller 38 and secondary feed roller 52, and additional material build-up sensors 94a, b, c are provided at each of the pressure rollers 44a, b, c and pressure rollers 60a, b, c. Suitable material buildup sensors 92 for the feed rollers 38 and 52 are commercially available from Banner Engine of Minneapolis, Minn. under Part No. SE61RNC and SE61E, and suitable material build-up sensors 94a, b, c for the pressure rollers 44a, b, c and 60a, b, c are commercially available from Turck, Inc. of Minneapolis, Minn. under Part No. BIM-IKT-AN6X/KLI-1. The function of the sensors 92, 94 is to detect the presence of an inordinate build up of tow strands 20 on the feed rollers 38, 52, or pressure rollers 44, 60, and send signals to the controller 28 through lines 96 connected to each sensor 92 and lines 98a, b, c connected to each set of sensors 94a, b, c.

As mentioned above, a loop 54 is preferably maintained in each of the tows 18a, b, c between the primary and secondary feed rollers 38, 52. In the presently preferred embodiment, three loop sensors 100 (only one of which is shown) connected by lines 102a, b, c to controller 28, is located between the feed rollers 38 and 52 to detect the presence of a loop 54 for each tow 18a, b, c. It is contemplated that these loop sensors 100 may be standard optical sensors, for example, or any other type of position sensor. One type of sensor which is suitable for this purpose is a measuring light curtain system available under the trade name "Beam-A-Ray" from Banner Engine of Minneapolis, Minn., Part No. BME/BMR.

With reference to the righthand portion of FIG. 1, two sets of sensors are associated with the venturi pump 22 and cutter mechanism 24 of this invention. In the presently preferred embodiment, a flow sensor 104a, b, c is mounted to the tow inlet tubes 72a, b, c, respectively, to detect motion of the tows 18a, b, c, therethrough. These sensors 104a, b, c are connected to controller 28 by separate lines 106a, b, c. Suitable sensors for this purpose are described below in connection with a discussion of venturi pump 22 and FIGS. 9 and 9A. Additionally, the outlet 82 of venturi pump 22 is equipped with a discharge flow sensor 108, connected by a line 109 to controller 28, for detecting the volume of chopped fibers 12 emitted from venturi pump 22. A sensor suitable for this purpose is shown in FIG. 9A and described below.

ALTERNATIVE EMBODIMENT OF FIG. 1A

Figure 1A:
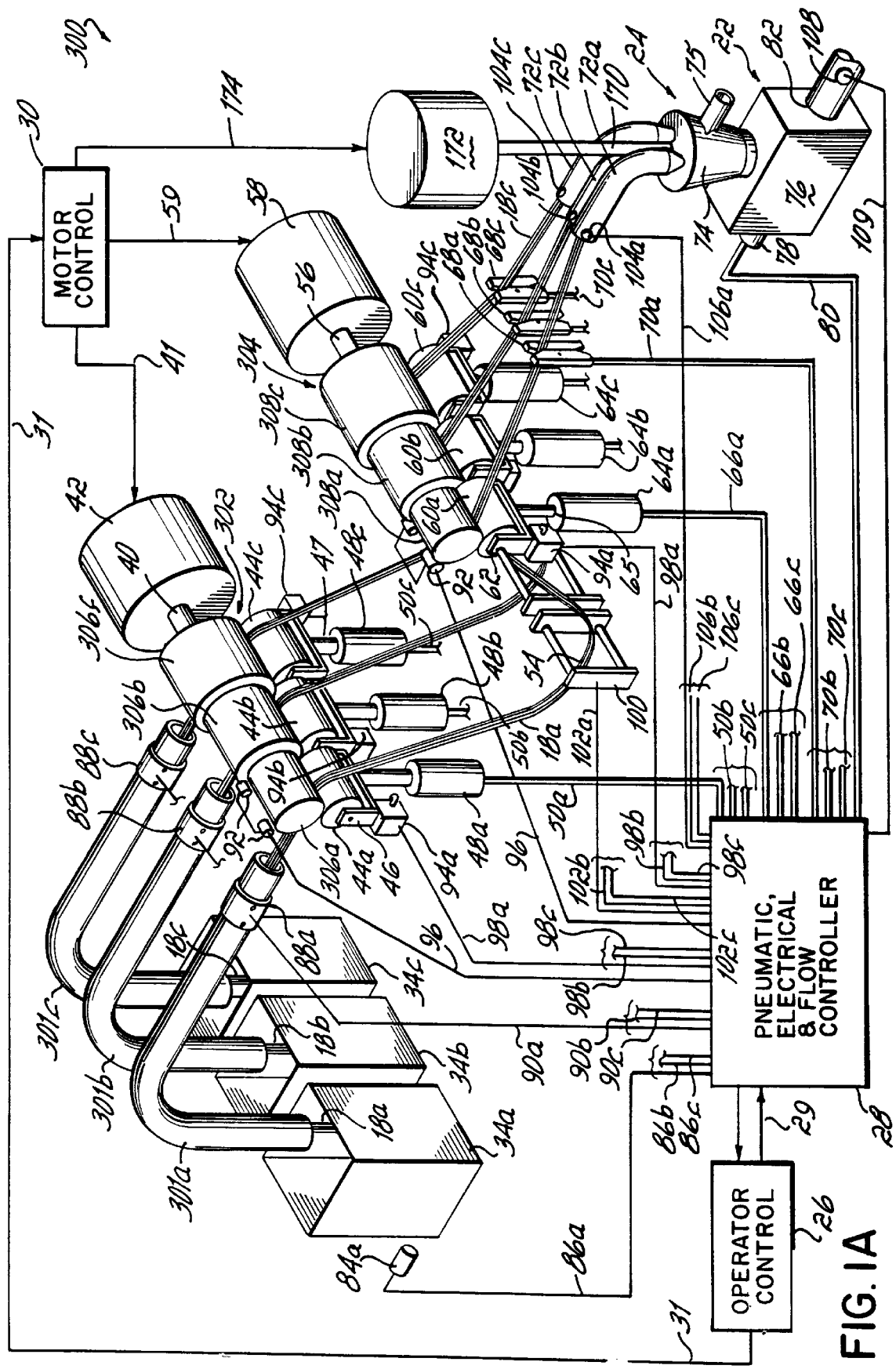
FIG. 1A is a schematic view of an alternative embodiment of the apparatus shown in FIG. 1.

With reference to FIG. 1A, an apparatus 300 is illustrated which is identical to apparatus 10 of FIG. 1 except the feed channels 36a, b, c are replaced with tubes 301a, b, c. A stepped, primary feed roller 302 is used in place of feed roller 38 and a stepped secondary feed roller 304 is used in place of feed roller 52. The stepped primary feed roller 302 has three sections 306a, b, c of progressively increasing diameter, and the secondary feed roller 304 is formed with three identical sections 308a, b and c. The tows 18a, b, c are first directed from the tubes 301a, b, c to the roller sections 306a, b, c of the stepped feed roller 302 where they are contacted by the pressure rollers 44a, b, c. The cylinder rod of each cylinder 48a, b, c is extended to the appropriate height so that the associated pressure rollers 44a, b, c connected thereto contact the tows 18a, b, c, respectively. The tows 18a, b, c are then fed to the respective sections 308a, b, c of secondary feed roller 304 where they are contacted by pressure rollers 60a, b and c extended into position by their associated cylinders 64a, b, c. Each of the individual sections 306a, b, c of the primary feed roller 302 and sections 308a, b, c of secondary feed roller 304 is provided with a separate material build-up sensor 92, only one of which is shown in FIG. 1A for sections 306a and 308a.

As discussed in detail below in connection with a description of the operation of this invention, the provision of sections 306a, b, c and 308a, b, c of different diameter along the feed rollers 302, 304, respectively, results in the formation of chopped fibers 20 of different length from each tow 18a, b and c because the different diameters of such sections 306a, b, c and 308a, b, c causes a different quantity of material to be advanced to the cutter mechanism 24.

Cutter Mechanism

Referring now to FIGS. 2–8, the cutter mechanism 24 of this invention is illustrated in detail. The cutter mechanism 24 is carried within a recess defined by an annular lip 110 at the top of the inlet cone 74 mounted to the pump body 76 of venturi pump 22. The inlet cone 74 is also formed with another inlet 75 which is adapted to connect to a source of lubricant, deodorant material or the like (not shown). The cutter mechanism includes a cover plate 112 which mounts three, tapered tow guide tubes 114a, b, c each joined by a connector 116 to the tow inlet tubes 72a, b, c, respectively. See also FIG. 1. An elongated, air inlet slot 118 is formed in the cover plate 112 adjacent each of the guide tubes 114a, b, c, and the cover plate 112 is also formed with a central throughbore 120. Mounting holes 122 for screws or the like are formed in the cover plate 112 for supporting the assembled cutter mechanism 24 on the annular lip 110 of the pump inlet cone 74.

The cover plate 112 fits atop a cutter plate 124 having a top surface 126 and a bottom surface 128. The cutter plate 124 is formed with a stepped throughbore 130 at its center, and three, rectangular-shaped tow slots 132a, b, c which are spaced approximately 120° from one another. These tow slots 132a, b, c align with the outlets of guide tubes 114a, b, c mounted on cover plate 112. An air slot 133 is formed in the cutter plate 124 adjacent each of the tow slots 132a, b, c, and these air slots 133 align with the slots 118 formed in the cover plate 112. Preferably, the stepped throughbore 130 mounts a bearing 134 and a thrust washer 136 for purposes described below. Cutter plate 124 is also formed with mounting holes 138 which align with the mounting holes 122 of cover plate 112.

Figure 2:
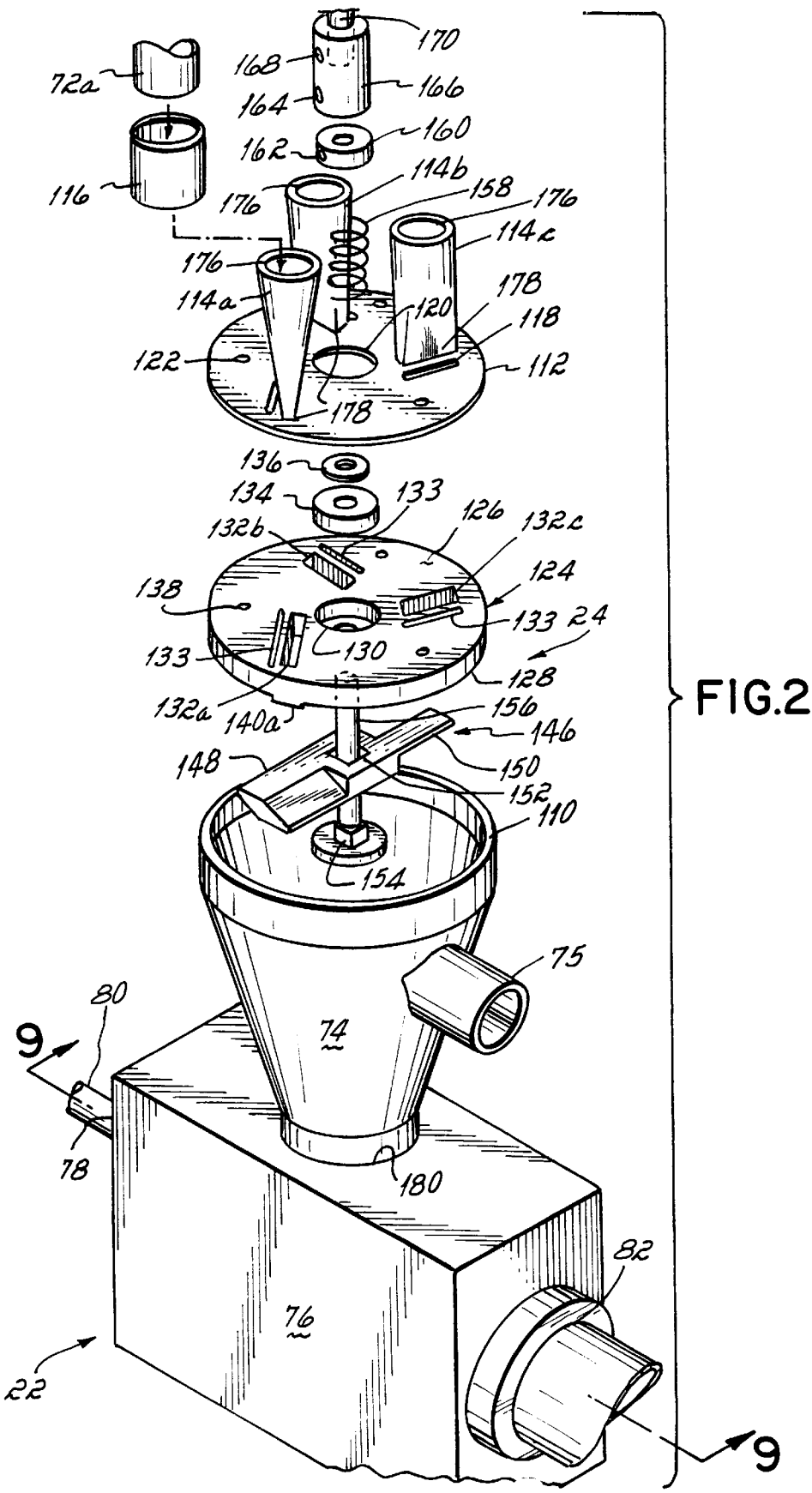
FIG. 2 is a disassembled perspective view of the cutter mechanism herein mounted to the venturi pump.

As best seen in FIGS. 2 and 8, three protrusions or ribs 140a, b, c, spaced 120° apart, extend outwardly from the bottom surface 128 of cutter plate 124 and are joined at the center thereof. The rectangular-shaped tow slots 132a, b, c extend through these ribs 140a, b, c, respectively, forming a shear edge 144 in each rib 140a, b, c which assist in the tow cutting operation described below.

Located adjacent the bottom surface 128 of cutter plate 124 is a double-edged cutter blade 146 having two cutting edges 148 and 150 oriented 180° from one another. The cutter blade 146 is formed with a square throughbore 152 which mates with the square base 154 of a blade drive shaft 156. As described in more detail below, the cutter blade 146 is rotatable with respect to the ribs 140a, b, c at the bottom of cutter plate 124 to shear the tows 18a, b, c as they pass through tow slots 132a, b, c against the shear edge 144 of the ribs 140a, b, c to form chopped fibers 12. Because the double-edge cutting blade 146 has cutting edges spaced 180° apart, and the ribs 140a, b, c of cutter plate 124 are spaced 180° from one another, chopped fibers 12 are formed at each 60° of rotation of the cutting blade 146. This produces a steady, essentially continuous supply of chopped fibers 12 of uniform length from each tow 18a, b, c for discharge from the venturi pump 22 as described below.

In assembling the cutter mechanism 24, the blade drive shaft 156 extends upwardly through the square throughbore 152 so that its square base 154 mates with the square throughbore 152 in cutter blade 146. The blade drive shaft 156 passes through the stepped throughbore 130 in cutter plate 124 to receive the bearing 134 and thrust washer 136 carried therein. The blade drive shaft 156 then extends through the central throughbore 120 of cover plate 112, and a compression spring 158 is placed over the blade drive shaft 156 between the thrust washer 136 seated on top of bearing 134 within the stepped throughbore 130 in cutter plate 124 and a spring locking ring 160. This spring locking ring 160 has a set screw 162 to support it on the blade drive shaft 156. By adjusting the position of the spring locking ring 160 along drive shaft 156, the upwardly directed force exerted by the spring 158 on the blade drive shaft 156 is varied thus altering the pressure with which the cutter blade 146 engages the ribs 140*a, b, c* of cutter plate 124. The upper end of blade drive shaft 156 is mounted by a set screw 164 within a collar 166. This collar 166 has a set screw 168 which mounts the drive shaft 170 of a variable speed cutter motor 172 connected by line 174 to the motor control 30. Rotation of the motor drive shaft 170 is transmitted through collar 166 to the blade drive shaft 156, which, in turn, rotates the cutter blade 146 along the bottom surface 128 of cutter plate 124 relative to the ribs 140*a, b, c* extending therefrom.

Several aspects of the operation of cutter mechanism 24 are important in obtaining clean and accurate cutting of the tows 18*a, b, c* to form chopped fibers 12 which are substantially uniform in length and which can be transmitted without bunching up through the venturi pump 22. One important feature of the cutter mechanism 24 is the configuration of the guide tubes 114*a, b, c*. As viewed in FIGS. 2–6, each guide tube 114*a, b, c* has a generally circular inlet 176, and a rectangular-shaped outlet 178. These outlets 178 have substantially the same dimensions, and are located in alignment with, the tow slots 132*a, b, c* in the cutter plate 124. Each guide tube 114*a, b, c* tapers radially inwardly from its inlet 176 to the rectangular-shaped outlet 178 for the specific purpose of spreading or flattening the tows 18*a, b, c* in the course of passage therethrough. As viewed in FIG. 4, the tow 18*a*, for example, has a generally circular cross section when it initially enters the inlet 176 of guide tube 114*a* wherein the individual strands 20 forming tow 18*a* are bunched together. In the course of passage through guide tube 114*a*, the tow 18*a* is formed to open or spread out in a generally elliptical shape. See FIG. 5. As viewed in FIG. 5, the individual strands 20 begin to separate from one another within the tow 18*a* and move into a side-by-side relationship. When the tow 18*a* reaches the rectangular-shaped outlet 178 of guide tube 114*a*, the individual strands 20 are separated even further from one another and are more nearly oriented side-by-side as compared to their relative position upon entry into guide tube 114*a*. See FIG. 4. The same is true for tows 18*b* and *c*.

The purpose of separating the individual strands 20 of tows 18*a, b, c*, and orienting them generally side-by-side, is to obtain a relatively precise cut of each tow. If the individual strands 20 are bunched up and stacked behind one another, i.e., as they would be if cut when oriented as in FIG. 4, the individual strands 20 tend to be crushed against one another and not cleanly and individually sheared. By separating the individual strands 20 from one another and orienting them generally side-by-side, as viewed in the sequence of FIGS. 4–6, essentially each individual strand 20 is contacted by a cutting edge 148 or 150 (FIG. 8) thus ensuring clean separation of a chopped fiber 12 from the remainder of the tow 18*a* (and tows 18*b, c*), and the production of chopped fibers 12 of uniform length.

Another feature of the cutter mechanism 24 of this invention which comprises an important aspect of this invention is the configuration of the ribs 140*a, b, c* at the bottom of the cutter plate 124 and the construction of the cutter blade 146. Because the individual strands 20 of the tows 18*a, b, c* are very light and difficult to manipulate when cut, it has been found advantageous and important to cut all of the strands 20 within a given tow 18 simultaneously, and then provide a flow path for the newly formed chopped fibers 12 in a direction away from the cutter plate 124 and cutter blade 146 toward the outlet of the venturi pump 22. This is accomplished in the cutter mechanism 24 of this invention by the movement of the cutter blade 146 with respect to the tow slots 132*a, b, c* and ribs 140*a, b, c*. As shown in FIG. 8, the cutter blade 146 is mounted for rotation with respect to the ribs 140*a, b, c* of cutter plate 124 such that the cutting edges 148, 150 of cutter blade 146 are oriented substantially parallel to the shear edges 144 formed by the tow slots 132*a, b, c* in ribs 140*a, b, c* when cutting a given tow 18. Movement of either cutting edge 148 or 150 of the cutter blade 146 against the shear edge 144 therefore results in the simultaneous shearing or cutting of essentially all of the strands 20 within a given tow 18*a, b, c*, as opposed to, for example, a scissors-type cutting action in which the individual strands 20 would be cut one at a time.

The reason for cutting all of the strands 20 within a given tow 18 simultaneously is to avoid the formation of a gap or flow path between a cutting edge 148 or 150 of cutter blade 146 and the shear edge 144 formed by tow slots 132*a, b, c* in ribs 140*a, b, c*. If such a gap or space was allowed to form, and the individual strands 20 within the tows 18*a, b, c* were cut one at a time, the newly formed chopped fibers 12 would tend to move toward such open space or gap creating bunching of the chopped fibers 12 thereat. Because the tows 18*a, b, c* are opened in the course of passage through the guide tubes 114*a, b, c*, as discussed above, their individual strands 20 are relatively uniformly spread across essentially the entire length of one of the shear edges 144 of ribs 140*a, b, c* in preparation for cutting. As viewed in FIG. 8, for example, the vacuum applied by the venturi pump 22 within each tow slot 132*a, b, c*, in combination with the counter-clockwise movement of the cutter blade 146 with respect to such tow slots 132*a, b, c*, forces the individual strands 20 of tow 18*a* against the shear edge 144 of tow slot 132*a* immediately prior to a cutting operation. A small, uniform gap is therefore formed between the cutting edge 150 and shear edge 144 of rib 140*a*, while the remainder of the tow slot 132*a* in rib 140*a* is covered by the cutter blade 146. Immediately after the strands 20 of tow 18*a* are simultaneously cut, the vacuum within guide tube 114*a* and tow slot 132*a* is momentarily interrupted because the cutter blade 146 advances to a position in which it covers the entire tow slot 132*a*. With all of the chopped fibers 12 from tow 18*a* formed simultaneously, and with the entire tow slot 132*a* momentarily covered, essentially the only flow path for movement of the newly formed chopped fibers 12 is away from the cutter plate 124 and cutter blade 146 under the influence of the negative pressure produced by the venturi pump 22. As a result, the chopped fibers 12 are cleanly severed from tow 18*a* and substantially separated from another to prevent bunching up in the area of the cutter blade 146 and/or cutter plate 124. This ensures a substantially uniform and constant volume supply of chopped fibers 12 is discharged from the venturi pump 22.

While the configuration of the cutter mechanism 24 described above is effective to direct the chopped fibers 12 into the venturi pump 22, it is recognized that there may be at least some accumulation of chopped fibers 12 on the cutter blade 146. The inlet slot 118 in cover plate 112, and the aligning air slots 133 in cutter plate 124, collectively provide an air flow path for ambient air which is drawn by the venturi pump 22 onto the cutter blade 146 as it rotates. This air flow effectively cleans the cutter blade 146 of chopped fibers 12 which are then directed into the venturi pump 22 for discharge.

Venturi Pump

Referring now to FIGS. 9–13, the venturi pump 22 of apparatus 10 is illustrated in more detail. As mentioned above, the function of the venturi pump 22 is to create a continuous vacuum which draws the tows 18a, b, c from the secondary feed roller 52 into the cutter mechanism 24 to form the chopped fibers 12. The venturi pump 22 can also be operated intermittently, in sequence with the secondary feed roller 52 or 304, to provide a vacuum when the tows 18a, b, c are intermittently fed thereto. In either mode of operation, chopped fibers 12 are emitted from the outlet 82 of venturi pump 22 for supply to a system of the type schematically illustrated in FIG. 14 and described below.

In the presently preferred embodiment, the venturi pump 22 comprises a pump body 76 formed with an inlet passageway 180 which mounts the inlet cone 74 described above in connection with cutter mechanism 24. The inlet passageway 180 intersects a throughbore 182 formed in the pump body 76 having opposed ends which form the inlet 78 and outlet 82 of venturi pump 22.

In order to develop a negative pressure within the inlet passageway 180, a nozzle 194 is mounted at the inlet end of inlet passageway 180 and a venturi insert 184 having a venturi passageway 186 is mounted at its outlet end. A number of different configurations of nozzles are illustrated in FIGS. 9–12, each of which direct a stream of pressurized air past the inlet passageway 180 and into a venturi passageway 186 formed in the venturi insert 184. As shown in FIG. 9, the venturi insert 184 is preferably formed with a flange 187 which engages the pump body 76 so that the inner end 188 of the venturi passageway 186 within insert 184 extends into the throughbore 182 substantially flush with the inlet passageway 180, and so that the discharge outlet 190 of venturi passageway 186 extends outwardly from the pump body 76.

The nozzle 194 illustrated in FIG. 9 comprises a nozzle body 196 having an outer end formed with a flange 198 which rests against the pump body 76, and an inner end 200 which extends into the path of the inlet passageway 180. The nozzle body 196 is formed with a stepped, central throughbore 202, the inlet end of which is formed with an air inlet which is threaded to receive a fitting (not shown) connected to the air line 80 from controller 28. The nozzle 194 is effective to discharge a pressurized stream of air through its central throughbore 202, past the inlet passageway 180 and into the venturi passageway 186 of the venturi insert 184. This pressurized air stream creates a vacuum or negative pressure within inlet passageway 180 which is transmitted through inlet cone 74 to the guide tubes 114a, b, c associated with cutter mechanism 24 and the tow inlet tube 72a, b, c which receive the tows 18a, b, c from the secondary feed roller 52.

In an alternative embodiment illustrated in FIG. 9A, a modified venturi insert 320 is provided which mounts the discharge flow sensor 108. As mentioned above, the discharge flow sensor 108 is preferably of the same type as flow sensors 88a, b, c located upstream from the primary feed rollers 38 or 302 and the flow sensors 104a, b, c located upstream from the cutter mechanism 24 and venturi pump 22. As shown in FIG. 9A, the venturi insert 320 is a cylindrical-shaped tube, preferably formed of aluminum or other electrically conductive material, having a venturi passage 322 and an external flange 324. When connected to the venturi pump 22, the flange 324 of venturi insert 320 engages the pump body 76 so that the inner end 326 of the venturi passage 322 within the insert 320 extends into the throughbore 182 in the venturi pump body 76 substantially flush with the inlet passageway 180, and so that the discharge outlet 328 of venturi passage 322 extends outwardly from the pump body 76.

In the presently preferred embodiment, the flow sensor 108 comprises a hollow, cylindrical-shaped fitting 330 which is carried on the outer end of the venturi insert 320 as shown in FIG. 9A. An electrically conductive ring 332, preferably formed of aluminum or the like, is press fit into the fitting 330 and is sandwiched between a pair of non-conductive rings 334 and 336 preferably formed of nylon or other dielectric material. The non-conductive ring 334 abuts the outer end of venturi insert 320 and the non-conductive ring 336 abuts an electrically non-conductive conduit, hose or tube 338. The fitting 330 is formed with drilled and tapped holes, two of which overlie the venturi insert 320 and the other two of which overlie the tube 338. These holes receive set screws 342 which mount the fitting 330 to both the venturi insert 320 and tube 338.

In the presently preferred embodiment, a single drilled and tapped hole 344 is formed in approximately the center of fitting 330, in alignment with the conductive ring 332, and this hole 344 receives an electrical contact 346 connected by a line (109, (FIGS. 1, 1A and 9A) to the controller 28. In response to movement of the tows 18a, b, c or fibers 20 through the flow sensor 108, or flow sensors 88a, b, c and flow sensor 104a, b, c, an electrostatic charge is produced within the conductive insert 320 and conductive ring 332. This electrostatic charge, in essence, is grounded through the contact 346 and line (109, (FIGS. 1, 1A and 9A). The magnitude of the electrostatic charge produced within the insert 320 and ring 332 is indicative of the rate at which the tows 18a, b, c or fibers 20 pass through the flow sensor 108 and such charge is sensed by the controller 28 and compared to a predetermined value to ensure that the material passes through the flow sensor 108 at the desired rate.

Another embodiment of a nozzle 206 is illustrated in FIG. 10. Nozzle 206 comprises a nozzle body 208 formed with a flange 210 at one end which engages the pump body 76, and an elongated, nozzle tip 212 at the opposite or inner end. The nozzle body 208 and nozzle tip 212 are formed with a stepped throughbore 214 having a larger diameter inlet portion 216 including a threaded air inlet within the nozzle body 208, and a smaller diameter outlet portion 218 within the nozzle tip 212 which terminates at a discharge outlet 220. The nozzle 206 of FIG. 10 is oriented with respect to the pump body 76 shown in FIG. 9 such that its nozzle tip 212 extends into the venturi passageway 186 of venturi insert 184 when the nozzle 206 is mounted in place within the pump body 76. The nozzle 206 is connected to the air line 80 from controller 28, and is effective to direct a stream of pressurized air from the discharge outlet 220 of its nozzle tip 212 directly into the venturi passageway 186 of venturi insert 184 to create a negative pressure within the inlet passageway 180.

A still further embodiment of a nozzle 224 is illustrated in FIGS. 11 and 11A. Nozzle 224 comprises a nozzle body 226 having an outer end formed with a flange 228 and an inner, internally threaded end 230 which mounts a nozzle tip 232. The nozzle tip 232 includes a threaded flange portion 233 which mounts to the threaded end 230 of nozzle body 226, and a substantially cone-shaped extension 234. A central portion 235 of the nozzle body 226 extends beyond its outer end 230 and engages the cone-shaped extension 234 of nozzle tip 232, with an O-ring 236 being provided therebetween to create a seal. The nozzle body 226 is formed with a central throughbore 238 which is connected to a central throughbore or discharge passageway 240 formed in the cone-shaped extension 234. A second passageway 242 is formed in the nozzle body 226, substantially parallel to the central throughbore 238 therein, and this passageway 242 terminates in an annular chamber 244 formed in the flange portion 233 of the nozzle tip 232. The annular chamber 244 communicates with a plurality of outlet ports 248 formed in the flange portion 233 of nozzle tip 232 which are radially spaced from the central throughbore or discharge passageway 240 of the coneshaped extension 234 and are circumferentially spaced from one another. See FIG. 11A.

The central throughbore 238 and passageway 242 of nozzle body 226 are connected at their respective air inlets by lines (not shown) to the controller 28 to receive pressurized air therefrom. One stream of pressurized air passes through the central throughbore 238 in nozzle body 226, and the central throughbore or discharge passageway 240 in the coneshaped extension 234, directly into the venturi passageway 186 of venturi insert 184. Another stream of air is transmitted through the passageway 242 in nozzle body 226, into the annular chamber 244 in the flange portion 233 of nozzle tip 232 and then through the outlet ports 248 therein. This produces an essentially cylindrical-shaped stream of air which flows generally concentric to the cone-shaped extension 234 of nozzle tip 232 and to the stream of air discharged from the central throughbore 240 of extension 234. These two streams of air enter the venturi insert 184 and create a negative pressure within inlet passageway 180.

The nozzle 250 illustrated in FIG. 12 is similar to that of FIG. 11 except for the elimination of a central throughbore. Nozzle 250 comprises a nozzle body 252 having an outer end formed with a flange 254, and a threaded inner end 255 which mounts to a threaded flange portion 258 of a nozzle tip 256 having a cone-shaped extension 260. The nozzle body 252 is formed with a passage 262 having an inlet end formed with an air inlet which is connected to the pressurized air line connected to controller 28, and an inner end which communicates with a chamber 266 formed in the flange portion 258 of nozzle tip 256. A plurality of outlet ports 268 are formed in the flange portion 258, in communication with the chamber 266, and these outlet ports 268 are preferably radially spaced from the longitudinal axis of the cone-shaped extension 260 and are circumferentially spaced from one another in the same manner as depicted in FIG. 11A. Pressurized air is directed through the passage 262 from controller 28, enters the chamber 266 and is then discharged through the outlet ports 268 directly into the venturi passageway 186 of venturi insert 184.

The nozzles 194, 206, 224 and 250 illustrated in FIGS. 9–12, respectively, are examples of presently preferred embodiments of a means for directing a stream of pressurized air past the inlet passageway 180 of venturi pump 22 and into the venturi insert 184, or, alternatively, a non-venturi discharge tube 270 of the type schematically depicted in FIG. 13. In addition to the creation of negative pressure within the inlet passageway 180, each of these nozzles is intended to provide an air flow within the inlet passageway 180, throughbore 182 and the venturi passageway 186 of venturi insert 184 which assists in creating at least some aeration and separation between the individual chopped fibers 12 produced by the cutter mechanism 24. Such separation is advantageous in order to reduce bunching up of the chopped fibers 12 and obtain a relatively constant flow rate or volume of chopped fibers 12 discharged from the venturi pump 22.

It is contemplated that the different configurations of the nozzles herein are more advantageously utilized in different spraying conditions. For example, the nozzles 194 and 206 illustrated in FIGS. 9 and 10 may be more useful in applications where greater feed rates of the chopped fibers 12 are required. On the other hand, nozzles 224 and 250 of FIGS. 11 and 12 may be more advantageously used in lower volume applications. It should be understood that the various configurations of the nozzles illustrated in FIGS. 9–12 are not intended to be exhaustive, but are given as examples of configurations which are useful in the venturi pump 22 to convey chopped fibers 12 of the type discussed herein.

Operation of System

For purposes of the present discussion, the operation of apparatus 10 is described in connection with the supply of highly moisture-absorbent chopped fibers 12 into a forming chamber 272 of the type used to make the nonwoven layer or pad 14 of a disposable diaper. The details of forming chamber 272 are disclosed in U.S. Pat. Nos. 4,927,346 and 5,017,324, assigned to the assignee of this invention, the disclosures of which are incorporated by reference in their entireties herein. Briefly, the forming chamber 272 includes an inlet 274 and an outlet 276. The conveyor 32, mentioned above, is preferably an endless perforated conveyor, carried by three rollers 280a, b, c, which is movable through the forming chamber 272 between its inlet 274 and outlet 276 in the direction indicated by the arrows in FIG. 14. The conveyor 32 is movable over a duct 282 mounted at the base of forming chamber 272 which is connected to a vacuum source 284.

Figure 14:
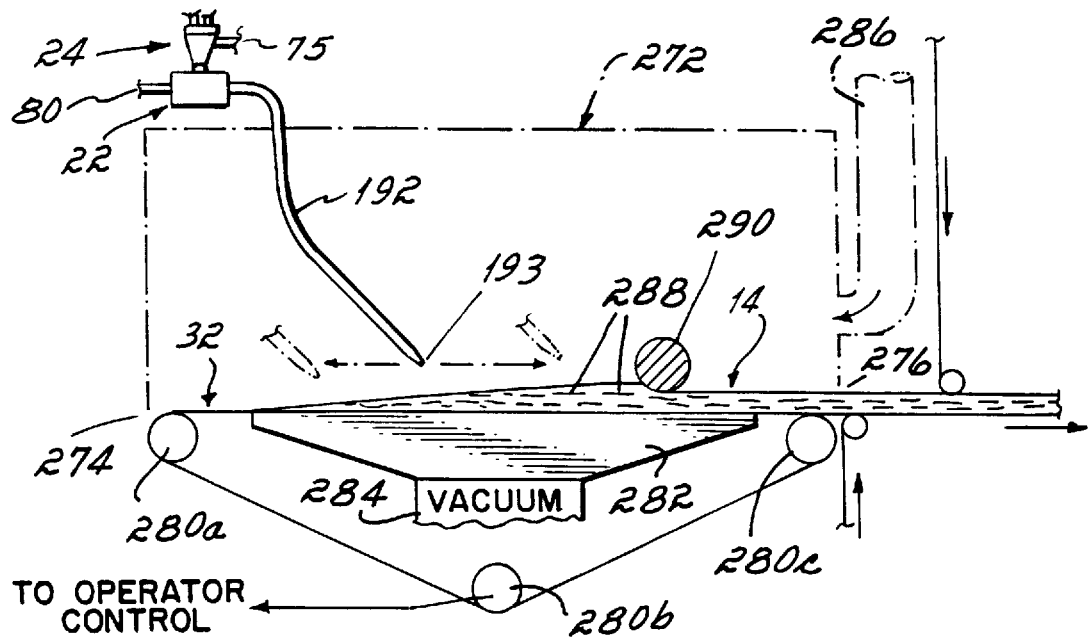
FIG. 14 is a schematic, elevational view of a portion of the apparatus of FIG. 1, adapted for use with a forming chamber employed to make the nonwoven pad of the hygienic article.
Figure 15:
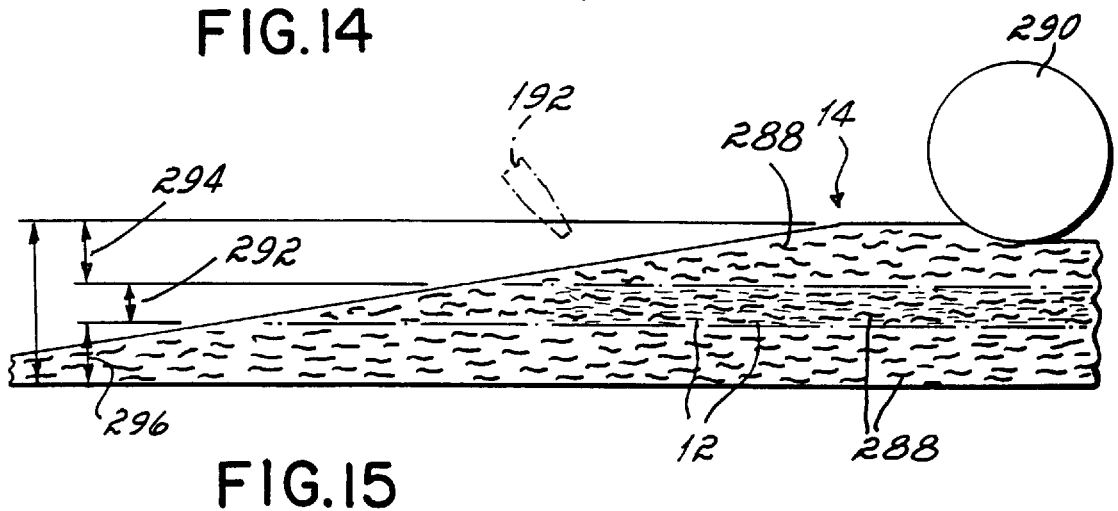
FIG. 15 is an enlarged, partial view of the nonwoven pad being formed within the forming chamber illustrated in FIG. 14.

A nonwoven material supply conduit 286 is connected to the conveyor outlet end of forming chamber 272 at a position above the conveyor 32. The conduit 286 is connected to a source (not shown) of fibrous material, preferably in the form of fibers or fluff 288 such as cellulose fluff, wood pulp, textile fibers or other fibrous material. The fluff 288 is pulled into the forming chamber 272 and drawn onto the conveyor 32 by operation of the vacuum source 284. As illustrated in FIGS. 14 and 15, vacuum is applied within the duct 282 which causes the fluff 288 to be drawn onto the conveyor 32 between the inlet end of forming chamber 272, where the duct 282 begins, and the outlet end of forming chamber 272 where the duct 282 ends. As the conveyor 32 moves through the forming chamber 272, the thickness of the intertwined fluff 288 drawn onto the conveyor 32 gradually increases from a point of minimum thickness near the chamber inlet 274 where the vacuum is initially applied, to a point of maximum thickness toward the chamber outlet 276. Preferably, a leveling or scarfing roller 290 is rotatably mounted within the forming chamber 272 near its outlet 276 to remove an upper portion of the fibers and form a nonwoven pad 14 having the desired finish thickness.

In this particular application of forming the nonwoven pad 14 of a disposable diaper within forming chamber 272, the apparatus 10 functions to introduce highly moisture-absorbent chopped fibers 12 into the forming chamber 272 where they are intermixed with a selected portion of the fluff 288 being drawn onto the conveyor 32 to form a nonwoven pad 14 in which the highly moisture-absorbent chopped fibers 12 are interspersed throughout a portion of the thickness of the pad 14 while maintaining other portions of the thickness of the pad 14 substantially free of chopped fibers 12. It can be appreciated that in the application of forming disposable diapers, a reliable, constant volume supply or quantity of chopped fibers 12 is critical in order to ensure that such pad 14 has the desired moisture-absorbency without introducing an inordinate amount of highly moisture-absorbent material therein.

The operation of the apparatus 10 depicted in FIG. 1 to achieve this end proceeds as follows. Initially, the speed of operation of apparatus 10 is correlated to the speed of the conveyor 32 moving through the forming chamber 272 so that the appropriate amount of chopped fibers 12 are supplied to the nonwoven pad 14 being formed within the forming chamber 272. The operator control 26 is provided for this purpose and controls the speed of the conveyor 32, as well as the operation of controller 28 and motor control 30 as described above. To begin operation, the operator control 26 signals controller 28 to operate the primary motor 42 driving primary feed roller 38 and the secondary motor 58 driving secondary feed roller 52 at the desired speeds. As described below, the pressure rollers 44a, b, c associated with primary feed roller 38, and the pressure rollers 60a, b, c associated with secondary feed roller 52, are all moved to their extended positions such that the tows 18a, b, c are forced against the primary and secondary feed rollers 38, 52 to positively feed them from their respective hoppers 34a, b, c to the cutter mechanism 24 of venturi pump 22. The venturi pump 22 operates to provide a continuous negative pressure or vacuum within the tow inlet tubes 72a, b, c and guide tubes 114a, b, c associated with cutter mechanism 24 such that the tows 18a, b, c are positively drawn from the secondary feed roller 52 into the cutter mechanism 24 and venturi pump 22. The cutting operation described below is performed by the cutter mechanism 24, and the chopped fibers 12 are then transmitted through and out of the venturi pump 22 as described below.

Figure 16:
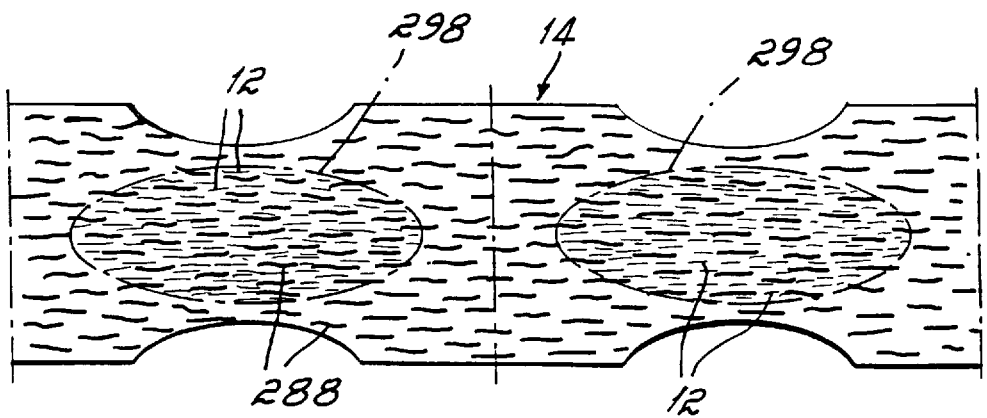
FIG. 16 is a plan view of a nonwoven pad made in the forming chamber of FIG. 14 wherein chopped fibers of moisture-absorbent material are disposed at selected areas along the length thereof.

In the embodiment of FIGS. 14–16, the chopped fibers 12 are discharged from the venturi pump 22 through a conduit 192 and into the forming chamber 272. As discussed in detail in U.S. Pat. Nos. 4,927,346 and 5,017,324, the outlet end 193 of conduit 192 is oriented with respect to the nonwoven fibers or fluff 288 being drawn onto the conveyor 32 such that the highly moisture-absorbent chopped fibers 12 are intermixed with a portion of the fluff 288 being drawn onto the conveyor 32 thus producing a nonwoven pad 14 in which the highly moisture-absorbent chopped fibers 12 are located in a predetermined portion 298 of the thickness of the pad 14. The portion of pad 14 in which the highly moisture-absorbent chopped fibers 12 and fluff 288 are intermixed is schematically illustrated as a thickness 292 in FIG. 15, whereas the areas 294 and 296 forming the remainder of pad 14 are substantially free of the highly moisture-absorbent chopped fibers 12.

It has been found that in the formation of a nonwoven pad 14 for disposable diapers, chopped fibers 12 of highly moisture-absorbent material provide a number of advantages. The chopped fibers 12 tend to become substantially intertwined with nonwoven fibers or the fluff 288 within the pad 14 which substantially reduces loss or migration of the highly moisture-absorbent material either through the perforated conveyor 32 within forming chamber 272 or at the outer surfaces of the nonwoven pad 14 such as against the polyethylene backing sheet (not shown) of a finished disposable diaper. Additionally, the chopped fibers 12 of highly moisture-absorbent material have a relatively large surface area, compared to highly moisture-absorbent material in particulate form, and therefore moisture or body fluids are readily and quickly absorbed by the highly moisture-absorbent fibers 12.

It should be understood that while the chopped fibers 12 are illustrated as being located predominantly within a center layer or area 292 within the thickness of the nonwoven pad 14, the chopped fibers 12 could be located essentially anywhere within the thickness of pad 14 as described in detail in U.S. Pat. Nos. 4,927,346 and 5,017, 324. Alternatively, the conduit 192 could be attached directly to the nonwoven material inlet conduit 286 such that the highly moisture-absorbent chopped fibers 12 are completely interspersed with the nonwoven material 288 as it enters the forming chamber 272, thus forming a nonwoven pad 14 in which the highly moisture-absorbent chopped fibers 12 are interspersed throughout the entire thickness of the nonwoven pad 14.

As mentioned above and schematically illustrated in FIG. 16, the apparatus 10 of this invention is capable of intermittently discharging chopped fibers 12 from the venturi pump 22. In order to obtain intermittent discharge of chopped fibers 12, the controller 28 signals motor control 30 to intermittently operate the secondary motor 58 associated with secondary feed roller 52. The secondary motor 58 is effective to start and stop the rotation of secondary feed roller 52 which controls the supply of tows 18a, b, c into the cutter mechanism 24 and venturi pump 22. The secondary feed roller 52 can be intermittently stopped and started without damaging tows 18a, b, c because of the excess length or loop 54 of each tow 18a, b, c formed between the primary feed roller 38 and secondary feed roller 52, described above. Accordingly, the tension of the tows 18a, b, c at the secondary feed roller 52 remains constant whether the secondary feed roller 52 is operated continuously or intermittently. If desired, the venturi pump 22 can also be operated intermittently, i.e., when the secondary feed roller 52 supplies the tows 18a, b, c thereto, so that a vacuum is always applied to the tows 18a, b, c when they are advanced from roller 52. Intermittent operation of secondary feed roller 52 produces a nonwoven pad 14 of the type shown in FIG. 16 wherein the highly moisture-absorbent chopped fibers 12 are located at longitudinally spaced areas 298 along the length of the pad 14.

It is contemplated that in most instances wherein the apparatus 10 is employed to form a nonwoven pad 14, the venturi pump 22 will be continuously operated. As a result, an essentially constant flow of air is introduced into the forming chamber 272, at a predetermined location relative to the nonwoven pad 14 being formed, which carries an intermittent supply of air-entrained chopped fibers 12. By providing a continuous air flow into the forming chamber 272, instead of an intermittent or pulsed flow of air-entrained chopped fibers 12, it is believed that there is less disruption in the movement of the fluff 288 onto the conveyor 32 and a more accurate distribution of chopped fibers 12 within the desired area or portion of the thickness of the nonwoven pad 14.

An important aspect of the operation of apparatus 10 is its capability of providing an essentially constant volume or quantity of chopped fibers 12 in the event the supply of one or more of the tows 18a, b, c is interrupted, terminated or otherwise varies from a predetermined feed rate. As discussed previously, the progress of each tow 18a, b, c through the apparatus 10 is individually monitored by a variety of sensors. Movement or flow sensors 88a, b, c are provided for each tow 18a, b, c upstream from primary feed roller 38, sensors 104a, b, c are located at the entrance to tow inlet tubes 72 and a flow sensor 108 is carried at the outlet 82 of pump body 76. Material level sensors 84a, b, c are provided for each tow 18a, b, c at their respective hoppers 34a, b, c, and a loop detection sensor 100 is provided for each tow 18a, b, c to detect the loop 54 thereof formed between the primary and secondary feed rollers 38, 52. Each of these sensors 88, 104, 108 and 100 provides signals to the controller 28 as described previously to monitor the feed/flow rate or movement of the tows 18a, b, c, or chopped fibers 12, compared to predetermined levels.

In the event of a termination, interruption or other variation in the supply of one or more of the tows 18, an operational sequence is initiated by controller 28 to maintain a substantially constant quantity of the chopped fibers 12, of the same length, for discharge through the venturi pump 22. For purposes of discussion, assume that the tow 18a has become severed somewhere in between its hopper 34a and the cutter mechanism 24. One or more of the sensors 88a, 100a, 104a or 108 will send a signal to the controller 28 indicating that the movement or flow of tow 18a has fallen below a predetermined level. Because one-third of the supply of material to the cutter mechanism 24 of venturi pump 22 is no longer present, the controller 28 is operative to "make up" or compensate for that loss by increasing the rate of supply of the other two tows 18b and c.

Initially, the controller 28 actuates the pneumatic clamp 68a associated with tow 18a to clamp the remainder of tow 18a in place upstream from the cutter mechanism 24 and venturi pump 22. The controller 28 signals motor control 30 to operate the primary motor 42 and secondary motor 58 which increase the speed of operation of the primary feed roller 38 and secondary feed roller 52, respectively. Assuming the same quantity of chopped fibers 12 is required, the speed of rotation of each of the primary and secondary feed rollers 38, 52 is increased fifty percent to make up for the loss of supply of tow 18a. In order to maintain the same length of chopped fibers 12 as had been obtained with all three tows 18a, b, c, the controller 28 signals the motor control 30 to speed up the operation of cutter motor 172. This increases the speed of rotation of the cutter blade 146 so that it is correlated with the increased speed of tows 18b and c passing through the cutter mechanism 24 and venturi pump 22. As a result, the chopped fibers 12 produced from only tows 18b and c are of substantially the same length as those produced when all three of the tows 18a, b, c are directed through cutter mechanism 24.

As mentioned below, material build-up sensors 92 are provided for each of the primary and secondary feed rollers 38, 52, and material build-up sensors 94a, b, c are provided for each of the pressure rollers 44a, b, c associated with primary feed roller 38 and each of the pressure rollers 60a, b, c associated with secondary feed roller 52. It is contemplated that in the event the individual strands 20 forming the tows 18a, b, c become adhered to either of the primary or secondary feed rollers 38, 52, as sensed by material build-up sensors 92, operation of apparatus 10 will have to be temporarily discontinued in order to clear such feed rollers 38, 52 of material. However, if a material build-up occurs on any one of the pressure rollers 44a, b, c or pressure rollers 60a, b, c, as sensed by material build-up sensors 94a, b, c, it is contemplated that a sequence of the type described above could be initiated. For example, if the pressure roller 44a associated with tow 18a became covered with material, the controller 28 would be operated to activate both pneumatic cylinders 48a and 64a to move the pressure roller 44a and 60a, respectively, to a retracted position away from their respective feed rollers 38, 52. The same sequence of operation with respect to the speed up of tows 18b and c and cutter motor 172 described above would then be initiated, while an operator was clearing either one of the pressure rollers 44a or 60a of material.

The apparatus 300 of this invention depicted in FIG. 1A operates in the identical manner as described above for apparatus 10 except for the relative quantities of chopped fibers 20 produced from each of the individual tows 18a, b and c. As discussed above, apparatus 300 differs from apparatus 10 in that a stepped primary feed roller 302 is provided having sections 306a, b and c of different diameter, and an identically configured stepped secondary feed roller 304 is provided with sections 308a, b and c. As depicted in FIG. 1A, the sections 306a, b and c of the primary feed roller 302 progressively increase in diameter so that in response to rotation of motor shaft 40 the smaller diameter section 306a rotates over a shorter distance, because of its smaller circumference, than the section 306b or section 306c. As a result, a greater quantity of tow 18c from the largest circumference section 306c passes to the cutter mechanism 24, compared to tows 18b and 18a, and the chopped fibers 20 produced from tow 18c are therefore longer than those produced from tow 18b, which, in turn, are longer than those produced from tow 18a.

The apparatus 300 of the embodiment of FIG. 1A therefore provides for the supply of different quantities of chopped fibers, having different lengths, depending upon the requirements of a particular application. For example, in the application of forming disposable diapers 14 it may be desirable to introduce different super-absorbent materials, each having different properties such as varying wicking capacity or the like, wherein it is preferred to have a larger quantity of one material than another. In such an application, one or more of the tows 18a, b and c could be formed of one type of super-absorbent material and another of the tows 18a, b, c could be formed of another super-absorbent material such that the desired relative quantity of such materials, in the form of chopped fibers 20 of different length, could be produced and dispensed from the venturi pump 22 into the forming chamber 272.

While the invention has been described with reference to a preferred embodiment, it should be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, the sequence of operation of apparatus 10 described above to accommodate the loss or interruption in the supply of one of the tows 18a involves an increase in feed rate of each of the other tows 18b and c to maintain a substantially constant feed rate or volume of chopped fibers 12 for discharge from the venturi pump 22. It is contemplated that such sequence of operation could also, or alternatively, include a slow down of the line speed of conveyor 32 within forming chamber 272, in the particular embodiment disclosed in FIG. 14, which would be effected by the operator control 26.

In addition, the cutter plate 124 is shown with a bottom surface 128 having three protrusions or ribs 140a, b, c against which the cutter blade 146 shears the tows 18a, b, c. It is contemplated that the bottom surface 128 could be flat, thus eliminating the ribs 140a, b, c, although the cutter blade 146 would essentially continuously rub or engage such surface and may wear more quickly.

The operation of apparatus 10 has also been described in connection with the supply of highly moisture-absorbent chopped fibers 12 into a forming chamber 272 having a conveyor 32. It should be understood that other forming chamber constructions could be employed, including those having a drum-type pad support.

Therefore, it is intended that the invention not be limited to the particular embodiment disclosed as the best mode contemplated for carrying out this invention, but that the invention will include all embodiments falling within the scope of the appended claims.

It is claimed:

1. A cutter plate adapted for use in a cutter mechanism which forms chopped fibers from continuous tows comprising:

a circular plate having first and second surfaces;

said circular plate being formed with at least two ribs extending outwardly from said second surface thereof;

said circular plate being formed with tow slot means, each extending from said first surface thereof through one of said ribs, said tow slot means each forming a straight shear edge along one of said ribs;

said tow slot means being disposed about an axis through said plate such that said shear edges are disposed about said axis and extend in a direction other than radially with respect thereto;

each said tow slot means for receiving and confining a plurality of fibers in one of said tows uniformly across said shear edges for shearing;

one of said tows slot means each being adapted to receive a tow which passes therethrough and protrudes beyond said ribs extending from said second surface of said circular plate in position with respect to said straight shear edge of said ribs so that a cutter blade having a cutting edge parallel to said shear edges when shearing said fibers, can cut the tow against said shear edge to form chopped fibers.

2. The cutter plate of claim 1 in which said circular plate is formed with three of said tow slot means, wherein the tow slot means are rectangular-shaped and spaced 120° from one another.

3. The cutter plate of claim 2 in which said circular plate is formed with air discharge means adjacent each of said tow slot means for directing a stream of air to remove chopped fibers from the cutter blade.

4. A cutter plate adapted for use in a cutter mechanism which forms chopped fibers from continuous tows comprising:

a circular plate having first and second surfaces;

said circular plate being formed with at least two tow slots each extending from said first surface to said second surface thereof, said tow slots each forming a shear edge along said second surface of said circular plate;

said tow slots each respectively receiving a tow which passes therethrough and protrudes beyond said second surface of said circular plate in position with respect to said shear edge of each of said tow slots so that a cutter blade can cut said tow against said shear edge to form chopped fibers;

said circular plate being formed with air discharge means, located adjacent each of said tow slots, for directing a stream of air in a direction to remove chopped fibers from the cutter blade.

5. The cutter plate of claim 4 in which said circular plate is formed with at least two ribs extending outwardly from said second surface thereof, said tow slots each extending from said first surface through one of said ribs to form said shear edge therealong.

6. The cutter plate of claim 4 in which said air discharge means comprises an elongated slot extending between said first and second surfaces of said cutter plate adjacent each of said tow slots.

7. A cutter assembly adapted for use with a cutter mechanism which forms chopped fibers from continuous tows formed of individual strands, comprising:

a circular plate having a first surface and a second surface, said circular plate being formed with at least two ribs extending outwardly from said second surface thereof and at least two tow slots each extending from said first surface through one of said ribs, each of said tow slots forming a straight shear edge along one of said ribs for receiving a tow;

each of said tow slots receiving uniformly spread individual strands of the tows along said shear edges;

a cutter blade operably mounted proximate said circular plate for rotation about an axis extending therethrough, and having at least one cutting edge which is movable with respect to said ribs of said circular plate so that said at least one cutting edge thereof passes in close shearing proximity to said straight shear edges formed along each of said ribs and simultaneously shears substantially all of the strands within tows extending respectively through said tow slots in said circular plate;

said straight shear edges being disposed about said axis in a direction other than radially with respect thereto, and said cutting edge being disposed in said blade such that said cutting edge is parallel to said shear edges when said cutting blade shears said strands across said shear edges.

8. The cutter assembly of claim 7 in which said at least two ribs comprises three ribs spaced 120° apart, and said at least one cutting edge of said cutter blade comprises two cutting edges spaced 180° apart.

9. Apparatus for chopping fibers from individual strands of at least one continuous tow, said apparatus comprising:

means for feeding at least one continuous tow to a tow guide, a cutter plate, a tow slot in said cutter plate, said tow guide being connected to and aligned with said tow slot, said tow slot defining a straight shear edge at a surface of said cutter plate, a knife mounted adjacent said cutter plate and having a cutting edge movable into parallel relation with said shear edge for cooperating with said shear edge to chop said fibers from said strands, a housing for said cutter plate surface and said knife, an outlet from said housing for dispensing chopped fibers, and pump means for creating a suction in said housing and in said tow guide, and for sucking said chopped fibers from said housing;

wherein said pump means creates a suction in said tow guide and wherein said knife includes a surface for blocking said tow slot after said knife chops said fibers from said at least one continuous tow for transporting said chopped fibers away from said knife;

and further including air slots in said cutter plate for passing air into said housing.

10. A cutter mechanism for forming chopped fibers from continuous tows formed of a plurality of strands, comprising:

a cutter plate having a first surface and a second surface, said cutter plate being formed with first and second tow slot means each extending from said first surface to said second surface, and each defining, with one of said surfaces, a straight shear edge;

each said tow slot means for receiving and confining a plurality of individual strands of said tows uniformly across said straight shear edges;

first and second guide tubes each having an inlet and an outlet aligned with said first and second tow slot means, respectively, in said cutter plate, said first and second guide tubes tapering inwardly from said inlet to said outlet thereof so that the individual strands of a first tow and a second tow are at least partially separated from one another and oriented generally side-by-side in the course of passage through said first and second guide tubes and prior to entry into said first and second tow slot means formed in said cutter plate;

a cutter blade operably mounted on an axis extending through said cutter plate and proximate said one of said surfaces of said cutter plate and having at least one cutting edge, said cutter blade being rotatable with respect to said cutter plate so that said at least one cutting edge thereof shears substantially all of said strands within said first and second tows at said first and second tow slot means to form said chopped fibers;

said straight shear edges being disposed about said axis in a direction other than radially with respect thereto; and said cutting edge being disposed in said blade such that said cutting edge is parallel to said shear edges when said cutting blade shears said strands across said shear edges.

11. The apparatus of claim 10 in which said cutter plate is formed with first and second ribs extending outwardly from said second surface thereof, said first and second tow slot means each extending from said first surface through said first and second ribs, respectively.

12. The apparatus of claim 11 in which each of said first and second tow slot means is rectangular in shape forming an elongated straight shear edge in each of said first and second ribs, said cutter blade being movable relative to said rectangular tow slot means in each of said first and second ribs such that said cutting edge of said cutter blade is oriented substantially parallel to said elongated straight shear edge of said rectangular tow slots upon cutting of said first and second tows while the remainder of said rectangular tow slot in each of said first and second ribs is substantially covered by said cutter blade to prevent the passage of pressurized fluid therethrough.

13. The apparatus of claim 10 in which said cutter plate is formed with an air discharge means adjacent each of said first and second tow slot means for directing a stream of air to remove chopped fibers from said cutter blade.

14. The apparatus of claim 10 further including a third tow, a third guide tube and a third tow slot means in said cutter plate, said first, second and third guide tubes and tow slot means respectively being spaced approximately 120° from one another.

15. The apparatus of claim 14 in which said at least one cutting edge of said cutter blade comprises two cutting edges spaced 180° apart, said cutter blade being rotatable with respect to said cutter plate so that chopped fibers are produced from said first, second and third tows at each 60° of rotation of said cutter blade.

* * * * *